(12) United States Patent
Zdeblick

(10) Patent No.: US 8,644,919 B2
(45) Date of Patent: Feb. 4, 2014

(54) SHIELDED STIMULATION AND SENSING SYSTEM AND METHOD

(75) Inventor: Mark Zdeblick, Portola Valley, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 0 days.

(21) Appl. No.: 12/595,033

(22) PCT Filed: Oct. 6, 2009

(86) PCT No.: PCT/US2009/059704
§ 371 (c)(1),
(2), (4) Date: Apr. 14, 2010

(87) PCT Pub. No.: WO2010/056438
PCT Pub. Date: May 20, 2010

(65) Prior Publication Data
US 2011/0282179 A1    Nov. 17, 2011

Related U.S. Application Data

(60) Provisional application No. 61/151,170, filed on Feb. 9, 2009, provisional application No. 61/114,441, filed on Nov. 13, 2008.

(51) Int. Cl.
*A61B 5/00*    (2006.01)

(52) U.S. Cl.
USPC .......................................... 600/547

(58) Field of Classification Search
USPC ........... 600/547, 372, 375, 377, 393; 607/5–8
See application file for complete search history.

(56) References Cited

U.S. PATENT DOCUMENTS

| | | | | |
|---|---|---|---|---|
| 4,413,346 A | * | 11/1983 | Palmquist | 373/41 |
| 4,835,423 A | * | 5/1989 | de Ferron et al. | 327/436 |
| 4,969,468 A | * | 11/1990 | Byers et al. | 600/373 |
| 4,985,619 A | * | 1/1991 | Arques | 250/208.1 |
| 5,068,622 A | * | 11/1991 | Mead et al. | 330/253 |
| 5,114,424 A | | 5/1992 | Hagen et al. | |

(Continued)

FOREIGN PATENT DOCUMENTS

| | | |
|---|---|---|
| EP | 0159753 | 10/1985 |
| EP | 1048321 | 11/2000 |

(Continued)

OTHER PUBLICATIONS

Kovacs, "Technology Development for a Chronic Neural Interface", A Dissertation, Stanford University Aug. 1990; pp. 9, 225-234, 257, 276.

*Primary Examiner* — Max Hindenburg
(74) *Attorney, Agent, or Firm* — Oppedahl Patent Law Firm, LLC

(57) ABSTRACT

Spatial arrays of electrodes are provided, each array in a region of tissue. The electrodes of an array are connected so that some of the electrodes serve as shield electrodes relative to a pair of electrodes used for pulse stimulation or sensing of electrical activity, or both. The shield electrodes are connected together, defining an electrical node, the node defining a stable potential in predetermined relationship with power supply levels or with reference voltages for sensing circuitry. Multiplexing techniques may be employed so that sensed activity at each of several electrode locations can be communicated to electronics external to the electrode locations.

15 Claims, 12 Drawing Sheets

(56) References Cited

U.S. PATENT DOCUMENTS

| | | | |
|---|---|---|---|
| 5,193,539 A | 3/1993 | Schulman et al. | |
| 5,328,442 A | 7/1994 | Levine | |
| 5,370,672 A | 12/1994 | Fowler et al. | |
| 5,400,784 A | 3/1995 | Durand et al. | |
| 5,509,410 A * | 4/1996 | Hill et al. | 600/393 |
| 5,526,808 A * | 6/1996 | Kaminsky | 600/370 |
| 5,724,984 A | 3/1998 | Arnold et al. | |
| 5,749,369 A * | 5/1998 | Rabinovich et al. | 600/547 |
| 5,769,877 A | 6/1998 | Barreras | |
| 5,788,692 A | 8/1998 | Campbell et al. | |
| 5,836,875 A | 11/1998 | Webster, Jr. | |
| 5,873,849 A | 2/1999 | Bernard | |
| 5,895,416 A | 4/1999 | Barreras et al. | |
| 5,916,158 A | 6/1999 | Webster, Jr. | |
| 5,938,596 A | 8/1999 | Woloszko et al. | |
| 5,938,690 A | 8/1999 | Law et al. | |
| 6,006,124 A | 12/1999 | Fischell et al. | |
| 6,024,702 A | 2/2000 | Iversen | |
| 6,061,593 A | 5/2000 | Fischell et al. | |
| 6,061,596 A | 5/2000 | Richmond et al. | |
| 6,064,905 A | 5/2000 | Webster, Jr. et al. | |
| 6,163,725 A | 12/2000 | Peckham et al. | |
| 6,167,311 A | 12/2000 | Rezai | |
| 6,241,724 B1 | 6/2001 | Fleischman et al. | |
| 6,259,937 B1 | 7/2001 | Schulman et al. | |
| 6,292,697 B1 | 9/2001 | Roberts | |
| 6,308,102 B1 | 10/2001 | Sieracki et al. | |
| 6,317,628 B1 * | 11/2001 | Linder et al. | 600/547 |
| 6,418,344 B1 | 7/2002 | Rezai et al. | |
| 6,459,745 B1 | 10/2002 | Moose et al. | |
| 6,473,653 B1 | 10/2002 | Schallhorn | |
| 6,519,488 B2 * | 2/2003 | KenKnight et al. | 600/372 |
| 6,570,144 B1 * | 5/2003 | Lee et al. | 250/208.1 |
| 6,600,954 B2 | 7/2003 | Cohen et al. | |
| 6,609,030 B1 | 8/2003 | Rezai et al. | |
| 6,609,031 B1 | 8/2003 | Law et al. | |
| 6,654,642 B2 | 11/2003 | North et al. | |
| 6,708,064 B2 | 3/2004 | Rezai | |
| 6,745,079 B2 | 6/2004 | King | |
| 6,748,276 B1 | 6/2004 | Daignault, Jr. et al. | |
| 6,793,801 B2 * | 9/2004 | Holland | 205/742 |
| 6,819,956 B2 * | 11/2004 | DiLorenzo | 607/45 |
| 6,856,822 B2 | 2/2005 | Larsson | |
| 6,871,099 B1 | 3/2005 | Whitehurst et al. | |
| 6,882,881 B1 | 4/2005 | Lesser et al. | |
| 6,895,280 B2 | 5/2005 | Meadows et al. | |
| 6,895,283 B2 | 5/2005 | Erickson et al. | |
| 6,993,384 B2 | 1/2006 | Bradley et al. | |
| 7,010,356 B2 | 3/2006 | Jog et al. | |
| 7,047,082 B1 | 5/2006 | Schrom et al. | |
| 7,047,084 B2 | 5/2006 | Erickson et al. | |
| 7,142,923 B2 | 11/2006 | North et al. | |
| 7,146,219 B2 | 12/2006 | Sieracki et al. | |
| 7,146,224 B2 | 12/2006 | King | |
| 7,174,218 B1 | 2/2007 | Kuzma | |
| 7,181,286 B2 | 2/2007 | Sieracki et al. | |
| 7,181,288 B1 | 2/2007 | Rezai et al. | |
| 7,214,189 B2 | 5/2007 | Zdeblick | |
| 7,216,000 B2 | 5/2007 | Sieracki et al. | |
| 7,231,254 B2 | 6/2007 | DiLorenzo | |
| 7,239,918 B2 | 7/2007 | Strother et al. | |
| 7,254,445 B2 | 8/2007 | Law et al. | |
| 7,292,890 B2 | 11/2007 | Whitehurst et al. | |
| 7,324,852 B2 | 1/2008 | Barolat et al. | |
| 7,330,764 B2 | 2/2008 | Swoyer et al. | |
| 7,333,857 B2 | 2/2008 | Campbell | |
| 7,337,006 B2 | 2/2008 | Kim et al. | |
| 7,346,398 B2 | 3/2008 | Gross et al. | |
| 7,349,743 B2 | 3/2008 | Tadlock | |
| 7,369,897 B2 | 5/2008 | Boveja et al. | |
| 7,373,206 B2 | 5/2008 | Sieracki et al. | |
| 7,386,348 B2 | 6/2008 | North et al. | |
| 7,395,118 B2 | 7/2008 | Erickson | |
| 7,403,820 B2 | 7/2008 | DiLorenzo | |
| 7,415,309 B2 | 8/2008 | McIntyre | |
| 7,447,546 B2 | 11/2008 | Kim et al. | |
| 7,450,993 B2 | 11/2008 | Kim et al. | |
| 7,467,016 B2 | 12/2008 | Colborn | |
| 7,502,651 B2 | 3/2009 | Kim et al. | |
| 7,580,753 B2 | 8/2009 | Kim et al. | |
| 7,809,444 B2 * | 10/2010 | Gibson et al. | 607/55 |
| 2001/0000187 A1 | 4/2001 | Peckham et al. | |
| 2001/0025192 A1 | 9/2001 | Gerber et al. | |
| 2002/0062141 A1 | 5/2002 | Moore | |
| 2002/0072770 A1 | 6/2002 | Pless | |
| 2002/0099419 A1 | 7/2002 | Cohen et al. | |
| 2002/0193859 A1 | 12/2002 | Schulman et al. | |
| 2003/0093130 A1 | 5/2003 | Stypulkowski | |
| 2003/0135248 A1 | 7/2003 | Stypulkowski | |
| 2004/0015205 A1 | 1/2004 | Whitehurst et al. | |
| 2004/0024440 A1 | 2/2004 | Cole | |
| 2004/0039417 A1 | 2/2004 | Soykan et al. | |
| 2004/0059392 A1 | 3/2004 | Parramon et al. | |
| 2004/0059395 A1 | 3/2004 | North et al. | |
| 2004/0093053 A1 | 5/2004 | Gerber et al. | |
| 2004/0098074 A1 | 5/2004 | Erickson et al. | |
| 2004/0193021 A1 | 9/2004 | Zdeblick | |
| 2004/0199235 A1 | 10/2004 | Younis | |
| 2005/0010262 A1 | 1/2005 | Rezai et al. | |
| 2005/0021103 A1 | 1/2005 | DiLorenzo | |
| 2005/0070982 A1 | 3/2005 | Heurth et al. | |
| 2005/0075681 A1 | 4/2005 | Rezai et al. | |
| 2005/0131506 A1 | 6/2005 | Rezai et al. | |
| 2005/0177192 A1 | 8/2005 | Rezai et al. | |
| 2005/0246004 A1 | 11/2005 | Cameron et al. | |
| 2005/0267542 A1 | 12/2005 | David et al. | |
| 2005/0283200 A1 | 12/2005 | Rezai et al. | |
| 2005/0283201 A1 | 12/2005 | Machado et al. | |
| 2005/0288760 A1 | 12/2005 | Machado et al. | |
| 2006/0004424 A1 | 1/2006 | Loeb et al. | |
| 2006/0020297 A1 | 1/2006 | Gerber et al. | |
| 2006/0058588 A1 | 3/2006 | Zdeblick et al. | |
| 2006/0085049 A1 * | 4/2006 | Cory et al. | 607/48 |
| 2006/0120013 A1 * | 6/2006 | Diorio et al. | 361/301.4 |
| 2006/0122654 A1 | 6/2006 | Bradley et al. | |
| 2006/0122678 A1 | 6/2006 | Olsen et al. | |
| 2006/0135862 A1 * | 6/2006 | Tootle et al. | 600/373 |
| 2006/0142802 A1 | 6/2006 | Armstrong | |
| 2006/0167525 A1 | 7/2006 | King | |
| 2006/0168805 A1 | 8/2006 | Hegland et al. | |
| 2006/0173262 A1 | 8/2006 | Hegland et al. | |
| 2006/0195145 A1 | 8/2006 | Lee et al. | |
| 2006/0212093 A1 | 9/2006 | Pless et al. | |
| 2006/0224222 A1 | 10/2006 | Bradley et al. | |
| 2006/0247539 A1 | 11/2006 | Schugt et al. | |
| 2006/0253182 A1 | 11/2006 | King | |
| 2006/0258950 A1 | 11/2006 | Hargrove et al. | |
| 2006/0263763 A1 * | 11/2006 | Simpson et al. | 435/4 |
| 2006/0265038 A1 | 11/2006 | Hagen et al. | |
| 2006/0270942 A1 * | 11/2006 | McAdams | 600/547 |
| 2007/0010858 A1 | 1/2007 | Forsberg | |
| 2007/0060970 A1 | 3/2007 | Burdon et al. | |
| 2007/0060980 A1 | 3/2007 | Strother et al. | |
| 2007/0060991 A1 | 3/2007 | North et al. | |
| 2007/0066995 A1 | 3/2007 | Strother et al. | |
| 2007/0067000 A1 | 3/2007 | Strother et al. | |
| 2007/0100399 A1 | 5/2007 | Parramon et al. | |
| 2007/0123944 A1 | 5/2007 | Zdeblick | |
| 2007/0123956 A1 | 5/2007 | Sieracki et al. | |
| 2007/0126024 A1 * | 6/2007 | Kelberlau | 257/173 |
| 2007/0162086 A1 | 7/2007 | DiLorenzo | |
| 2007/0167991 A1 | 7/2007 | DiLorenzo | |
| 2007/0168008 A1 | 7/2007 | Olsen | |
| 2007/0173896 A1 | 7/2007 | Zdeblick | |
| 2007/0173897 A1 | 7/2007 | Zdeblick | |
| 2007/0179569 A1 | 8/2007 | Zdeblick | |
| 2007/0179579 A1 | 8/2007 | Feler et al. | |
| 2007/0185537 A1 | 8/2007 | Zdeblick | |
| 2007/0185548 A1 | 8/2007 | Zdeblick | |
| 2007/0185549 A1 | 8/2007 | Zdeblick | |
| 2007/0198066 A1 | 8/2007 | Greenberg et al. | |
| 2007/0219608 A1 | 9/2007 | Swoyer et al. | |
| 2007/0255336 A1 | 11/2007 | Herbert et al. | |
| 2007/0255373 A1 | 11/2007 | Metzler et al. | |

(56) References Cited

U.S. PATENT DOCUMENTS

| | | |
|---|---|---|
| 2007/0265678 A1 | 11/2007 | Sieracki et al. |
| 2007/0282389 A1 | 12/2007 | Moxon et al. |
| 2007/0293906 A1 | 12/2007 | Cowan et al. |
| 2007/0293909 A1 | 12/2007 | Cowan et al. |
| 2007/0293910 A1 | 12/2007 | Strother et al. |
| 2007/0299483 A1 | 12/2007 | Strother et al. |
| 2008/0021292 A1 | 1/2008 | Stypulkowski |
| 2008/0021503 A1 | 1/2008 | Whitehurst et al. |
| 2008/0027289 A1 | 1/2008 | Zdeblick |
| 2008/0039916 A1 | 2/2008 | Colliou et al. |
| 2008/0045826 A1 | 2/2008 | Greenberg et al. |
| 2008/0046059 A1 | 2/2008 | Zarembo et al. |
| 2008/0058872 A1 | 3/2008 | Brockway et al. |
| 2008/0058899 A1 | 3/2008 | Sieracki et al. |
| 2008/0061630 A1 | 3/2008 | Andreu et al. |
| 2008/0065182 A1 | 3/2008 | Strother et al. |
| 2008/0077186 A1 | 3/2008 | Thompson et al. |
| 2008/0091246 A1 | 4/2008 | Carey et al. |
| 2008/0097529 A1 | 4/2008 | Parramon et al. |
| 2008/0097566 A1 | 4/2008 | Colliou |
| 2008/0114230 A1 | 5/2008 | Addis |
| 2008/0125833 A1 | 5/2008 | Bradley et al. |
| 2008/0132974 A1 | 6/2008 | Strother et al. |
| 2008/0139913 A1 | 6/2008 | Schulman |
| 2008/0140141 A1 | 6/2008 | Ben-David et al. |
| 2008/0140152 A1 | 6/2008 | Imran et al. |
| 2008/0140153 A1 | 6/2008 | Burdulis |
| 2008/0140167 A1 | 6/2008 | Hagen et al. |
| 2008/0140169 A1 | 6/2008 | Imran |
| 2008/0140170 A1 | 6/2008 | Filloux et al. |
| 2008/0147145 A1 | 6/2008 | Sieracki et al. |
| 2008/0147156 A1 | 6/2008 | Imran |
| 2008/0154328 A1 | 6/2008 | Thompson et al. |
| 2008/0154332 A1 | 6/2008 | Rezai |
| 2008/0167698 A1 | 7/2008 | Kim et al. |
| 2008/0177343 A1 | 7/2008 | Dal Molin et al. |
| 2008/0183221 A1 | 7/2008 | Burdulis |
| 2008/0183224 A1 | 7/2008 | Barolat |
| 2008/0183248 A1 | 7/2008 | Rezai et al. |
| 2008/0183257 A1 | 7/2008 | Imran et al. |
| 2008/0183258 A1 | 7/2008 | Inman |
| 2008/0188909 A1 | 8/2008 | Bradley |
| 2008/0208284 A1 | 8/2008 | Rezai et al. |
| 2008/0208305 A1 | 8/2008 | Rezai et al. |
| 2008/0215101 A1 | 9/2008 | Rezai et al. |
| 2008/0215125 A1 | 9/2008 | Farah et al. |
| 2008/0234791 A1 | 9/2008 | Arle et al. |
| 2008/0243214 A1 | 10/2008 | Koblish |
| 2008/0255647 A1 | 10/2008 | Jensen et al. |
| 2008/0294062 A1 | 11/2008 | Rapoport et al. |
| 2009/0024184 A1 | 1/2009 | Sun et al. |
| 2009/0112275 A1 * | 4/2009 | Cinbis et al. .................. 607/17 |
| 2010/0229642 A1 * | 9/2010 | Berndt et al. ............... 73/304 C |
| 2011/0007567 A1 * | 1/2011 | Modave et al. .......... 365/185.04 |

FOREIGN PATENT DOCUMENTS

| | | |
|---|---|---|
| EP | 1938861 | 7/2008 |
| JP | 9-501599 | 2/1997 |
| WO | WO 9952588 | 10/1999 |
| WO | WO 2004020040 | 3/2004 |
| WO | WO2004059392 | 3/2004 |
| WO | WO 2006073915 | 7/2006 |
| WO | WO2007070727 | 6/2007 |
| WO | 2007075974 | 7/2007 |
| WO | WO 2007075974 | 7/2007 |
| WO | 2007120884 | 10/2007 |
| WO | WO 2007120884 | 10/2007 |
| WO | WO 2008004010 | 1/2008 |
| WO | WO 2008008755 | 1/2008 |
| WO | WO 2008027639 | 3/2008 |
| WO | WO2008038208 | 4/2008 |
| WO | WO2009029894 | 3/2009 |

* cited by examiner

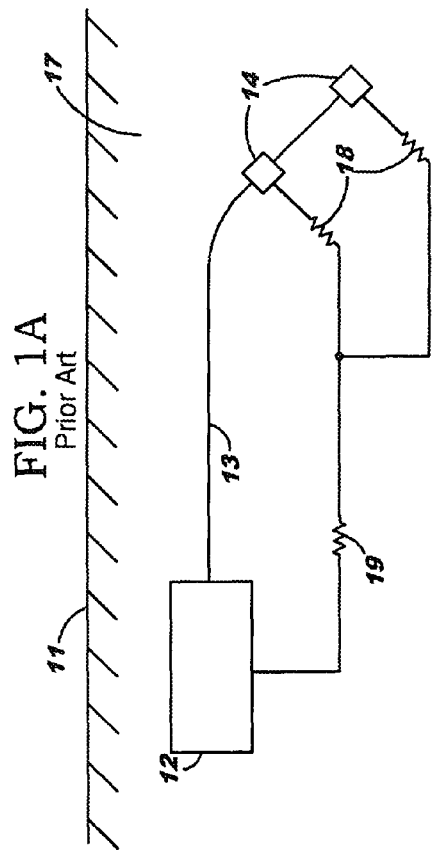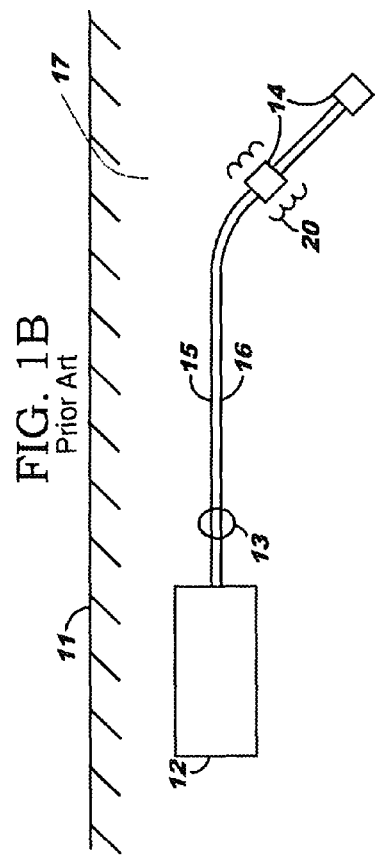

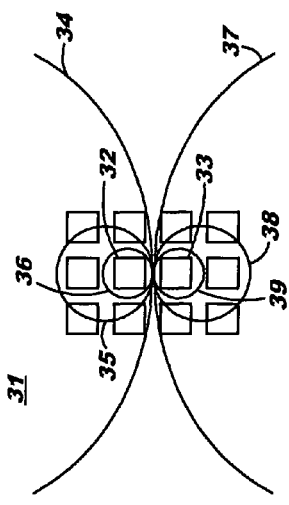
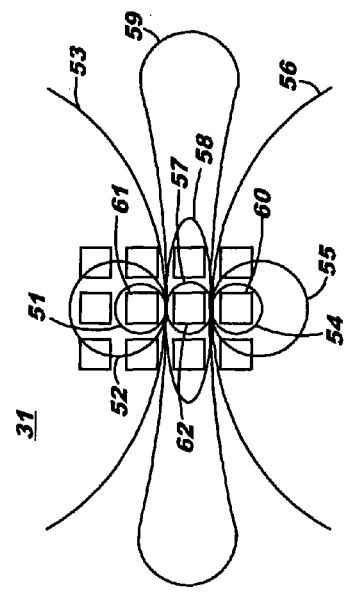
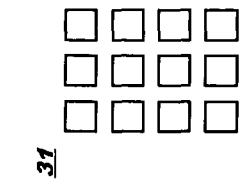
FIG. 2B
FIG. 2C
FIG. 2A

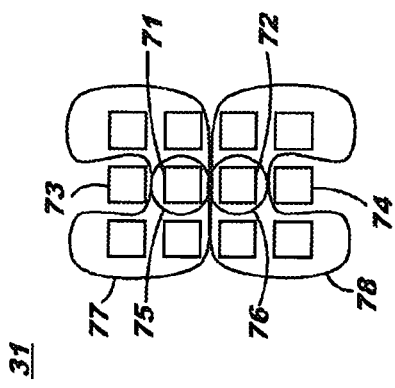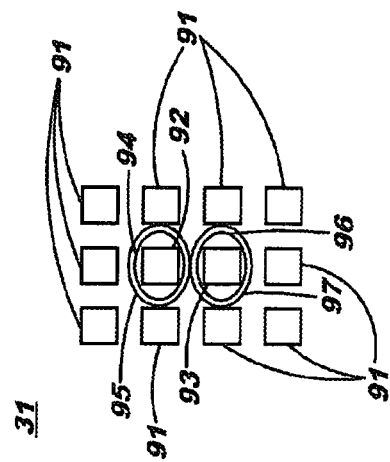

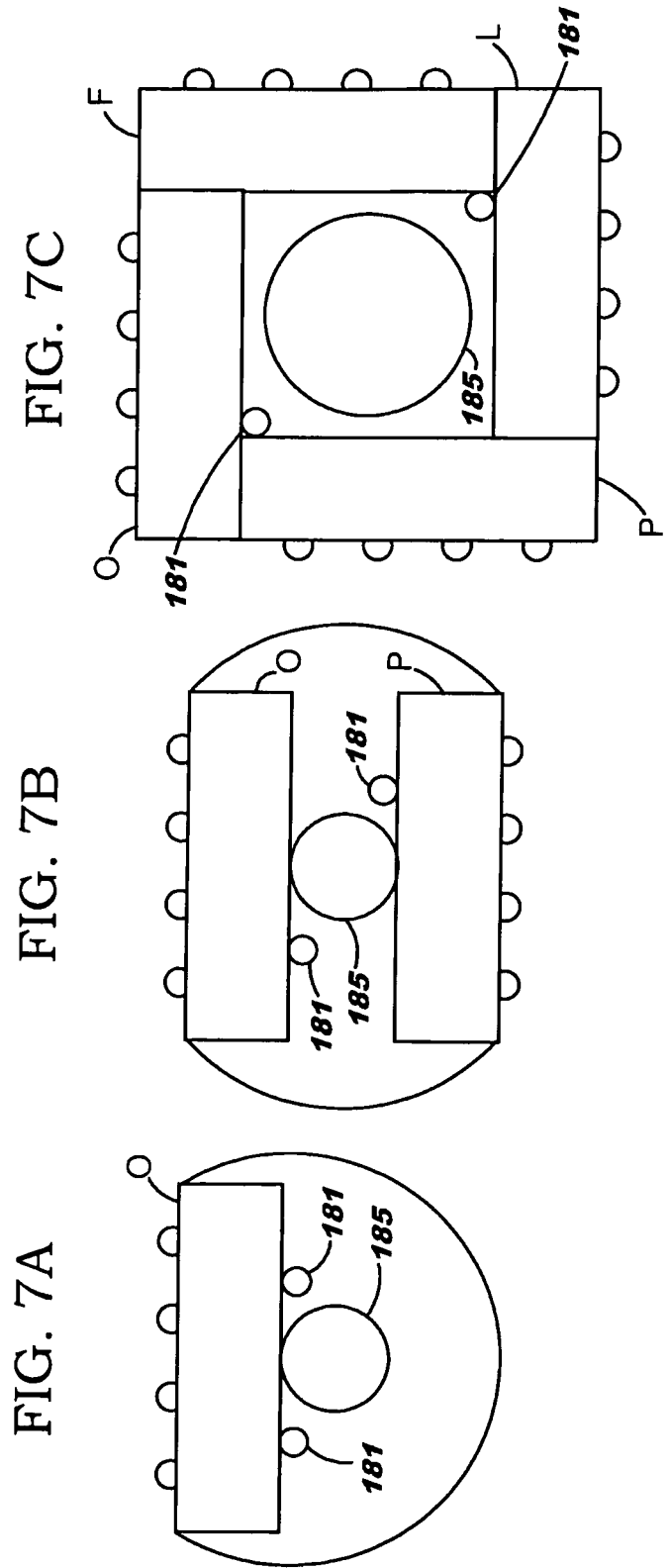

SHIELDED STIMULATION AND SENSING SYSTEM AND METHOD

This application claims the benefit of U.S. application No. 61/151,170 filed Feb. 9, 2009, and U.S. application No. 61/114,441 filed Nov. 13, 2008, each of which is incorporated herein by reference for all purposes.

BACKGROUND

It is not easy to sample electrical activity in very tightly defined areas of animal tissue, and it is not easy to stimulate very tightly defined areas of animal tissue. When further constraints are imposed, such as the desire to minimize trauma to the tissue in insertion of leads for such sampling and stimulation, and the need to be able to insert a lead only once and yet to preserve great flexibility in later use of the lead, the task that was not easy becomes even more difficult.

A prior-art type of stimulation and sensing is shown in FIGS. 1A and 1B. FIG. 1A shows a prior-art pacer lead configuration using a single conductor in a lead 13. The "can" 12 contains drive or sensing electronics that are external to electrode locations 14. The can 12 and lead 13 (with its electrode locations 14) is implanted within tissue 17 of an animal, below surface 11 such as a dermal surface.

An impedance model for the tissues 17 assumes localized impedances 18 physically nearby to the electrode areas 14, and more generalized impedance 19, together defining a return path to the can 12.

FIG. 1B shows a prior-art pacer lead configuration using two conductors 15, 16 in a lead 13. Electrodes at the electrode areas 14 may be selectively communicatively coupled with conductors 15, 16. Drive voltages from the can 12 pass through the conductors 15, 16 to particular electrodes in area 14. The drive voltage will stimulate a region 20 of the tissue 17.

The selective coupling of electrodes to lead conductors may be achieved for example by means of circuitry and techniques set forth in a multiplex system (e.g., as described in United States Patent publication no. US 20040254483 entitled "Methods and systems for measuring cardiac parameters"; US patent publication number US 20040220637 entitled "Method and apparatus for enhancing cardiac pacing"; US patent publication number US 20040215049 entitled "Method and system for remote hemodynamic monitoring"; US patent publication number US 20040193021 entitled "Method and system for monitoring and treating hemodynamic parameters; and provisional application No. 61/121,128 filed Dec. 9, 2008), which disclosures are hereby incorporated herein by reference for all purposes.

It will be appreciated that the same physical structures of these two figures may likewise be employed to permit sensing of electrical activity in particular regions of the tissue 17.

Experience shows that structures such as are portrayed here are well suited to stimulation or sensing of regions of tissue that are millimeters in size. For some applications such as cardiac pacing in human subjects, the millimeter-scale regions are exactly what is desired.

But for some diagnostic and therapeutic applications, it is needed or even required that the region of tissue being stimulated or sensed be on the order of a few hundred microns. If only ways could be found to stimulate and sense such very small regions, it might be possible to sense phenomena on the cellular level, perhaps as specific as the firing of an individual neuron. It might be possible to stimulate similarly small regions. Electrical stimulation might permit treatment, for example, of movement disorders such as Parkinson's and dystonia.

It would be highly desirable, however, that insertion of a lead for the purposes discussed here be done once and not more than once. Each insertion can cause trauma to tissue. If a lead were inserted, and later needed to be removed so that a different lead could be inserted (for example with a goal of slightly different electrode positioning) this would cause otherwise unneeded trauma to the nearby tissue. If on the other hand, a lead could be provided that permits great flexibility of use later, this would reduce how often a lead removal and replacement would be called for.

It is also highly desirable if such a lead could be as thin as possible, since a thinner lead is easier to insert and will cause less trauma to nearby tissue.

It has not, heretofore, been possible to achieve fully the desirable aims just discussed, particularly when other goals such as biocompatibility and physical reliability are also imposed.

SUMMARY OF THE INVENTION

Spatial arrays of electrodes are provided, each array in a region of tissue. The electrodes of an array are connected so that some of the electrodes serve as shield electrodes relative to a pair of electrodes used for pulse stimulation or sensing of electrical activity, or both. The shield electrodes are connected together, defining an electrical node, the node defining a stable potential in predetermined relationship with power supply levels or with reference voltages for sensing circuitry. Multiplexing techniques may be employed so that sensed activity at each of several electrode locations can be communicated to electronics external to the electrode locations.

DESCRIPTION OF THE DRAWING

The invention will be discussed and disclosed with respect to a drawing in several figures, of which:

FIG. 1A shows a prior-art pacer lead configuration using a single conductor in a lead;

FIG. 1B shows a prior-art pacer lead configuration using two conductors in a lead;

FIGS. 2A, 2B, 2C, 2D, and 2E show models for stimulation fields when various combinations of electrode selection and drive are employed;

FIGS. 7A, 7B, and 7C show exemplary positioning of integrated circuitry chips relative to conductors of a lead;

Where possible, like reference designations have been used among the figures to denote like elements.

DETAILED DESCRIPTION

Figure 3:
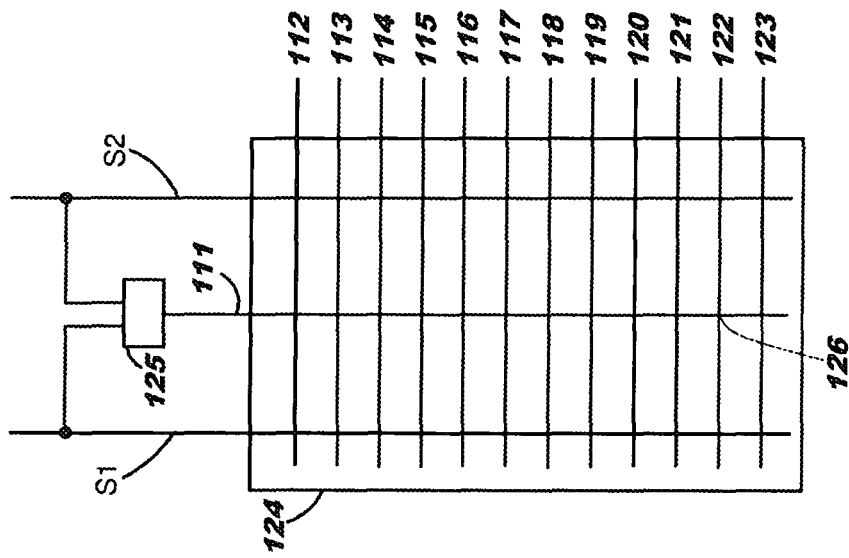
FIG. 3 shows an exemplary crosspoint matrix (switching fabric) that may be used in an integrated circuit chip according to an embodiment of the invention.

FIGS. 2A, 2B, 2C, 2D, and 2E show models for stimulation fields when various combinations of electrode selection and drive are employed.

FIG. 2A shows an exemplary array 31 of twelve electrodes in a 3 by 4 rectangular layout.

FIG. 2B models the situation when only two electrodes 32, 33 are energized, the other ten electrodes being permitted to "float" (at high impedance). In this figure it is assumed that the two driven electrodes are "floating", meaning that there is no particular "ground" reference (to body tissue) in the can 12.

Equipotential lines 39, 38, 37 and equipotential lines 36, 35, 34 are expected to be fairly symmetrical. On one model the voltage at 36 has dropped to around 37 percent of the voltage at electrode 32, and the voltage at 35 has dropped to around 24 percent of the voltage at electrode 32.

In the modeling of FIG. 2B, as in the modeling of subsequent figures, the percentages are of course a function of assumptions about tissue conductivity and physical dimensions. The relative levels of signal depicted in the various figures are thought to be at least approximate indicators of the effects associated with various electrode configurations.

FIG. 2C models the situation when electrodes 60, 61 are driven in one direction and electrode 62 is driven in the opposite direction. Again the other ten electrodes are at high impedance. In this figure it is assumed that the two drive levels are "floating", meaning that there is no particular "ground" reference (to body tissue) in the can 12.

The equipotential lines of this figure are expected to be fairly symmetrical both on a vertical axis centered in the figure, and on a horizontal axis passing through electrode 62. On one model the voltage at 52 has dropped to around 64 percent of the voltage at electrode 61, and the voltage at 53 has dropped to around 58 percent of the voltage at electrode 61.

FIG. 2D models the situation when electrodes 71, 72 are driven in opposite directions, and when two shield electrodes 73, 74 define a shield potential relative to a node (omitted for clarity in FIG. 2D) about which more will be said below.

The equipotential lines of this figure are expected to be fairly symmetrical both on a vertical axis centered in the figure, and on a horizontal axis centered in the figure. On one model the voltage at 77 has dropped to around 9 percent of the voltage at electrode 71, and the voltage at 73 has dropped to zero.

When one compares the modeled result in FIG. 2D (which has shield electrodes tied to a node as will be discussed) with the modeled results in FIG. 2A, 2B, or 2C, it becomes clear that the use of such shield electrodes can bring about an extremely well defined and small area in which the stimulation appears. Such stimulation might be deep brain stimulation, or spinal cord stimulation, or therapeutic stimulation for example for paralysis.

Likewise, although this discussion directs itself to stimulation, it will be appreciated that the use of such shield electrodes can bring about an extremely well defined and small area in which sensing takes place. Sensing might be used to measure chemicals and hormones such as GABA. Fiber optics might be used to check a spectrum of conductivity to determine changes in electro-conductivity of blood to identify levels of various chemicals such as GABA.

FIG. 2E models the situation when electrodes 92, 93 are driven in opposite directions, and when ten shield electrodes 91 define a shield potential relative to a node (omitted for clarity in FIG. 2E) about which more will be said below.

The equipotential lines of this figure are expected to be fairly symmetrical both on a vertical axis centered in the figure, and on a horizontal axis centered in the figure. On one model the voltage at a point that is three or four electrode spacings away has dropped to around 0.07 percent of the voltage at a driven electrode, and the voltage at any shield electrode 91 has dropped to zero. At a greater distance the model suggests the voltage may drop to 0.02 percent of the drive voltage.

When one compares the modeled result in FIG. 2E (which has shield electrodes tied to a node as will be discussed) with the modeled results in FIG. 2A, 2B, or 2C, it likewise becomes clear that the use of such shield electrodes can bring about an extremely well defined and small area in which the stimulation appears.

A typical chip might be 1.4 by 3.0 millimeters, with electrodes sensing at a cellular level with spatial definition in the nature of 100 microns.

FIG. 3 shows an exemplary crosspoint matrix (switching fabric) 124 that may be used in an integrated circuit chip according to an embodiment of the invention. Electrodes 112 through 123 are connected to this switching fabric. Leads S1 and S2 (comparable to conductors 15, 16 in FIG. 1B) also appear and connect to the fabric. An exemplary switch 126, along with thirty-five other switches left unlabeled for clarity in FIG. 3, provides the switching of the fabric. As a matter of terminology we will sometimes say that a particular electrode is "enabled" to one of the columns of the fabric, meaning that it is connected thereto.

In an exemplary embodiment each electrode such as 112 may be connected to S1, to S2, or to node 111, or may be at a high impedance. Additional columns may be provided for fabric 124 to permit selective connection of an electrode to a sensing circuit, or to permit selective connection of two electrodes to respective inputs of a differential amplifier, as will be described below. The node 111 may be thought of as a "floating node" in the sense that it is not tied metallically to any power supply line but is at some intermediate level. The intermediate level may move upward or downward as required to dissipate drive (stimulation) signals.

The electrodes together with the switching fabric may be conveniently be referred to as "multiplexed electrodes" in this context. Elsewhere in the discussion below, a multiplexing as between different integrated circuit chips (different electrode locations) may also be carried out.

Node 111 is important because it can provide a common connection point for a plurality of shield electrodes, so that differing potentials nearby to distinct shield electrodes will tend to be equaled out.

But node 111 is also important because it can be tied in a predefined way through circuitry 125 (about which more will be said below) to the conductors S1, S2.

Figure 4:
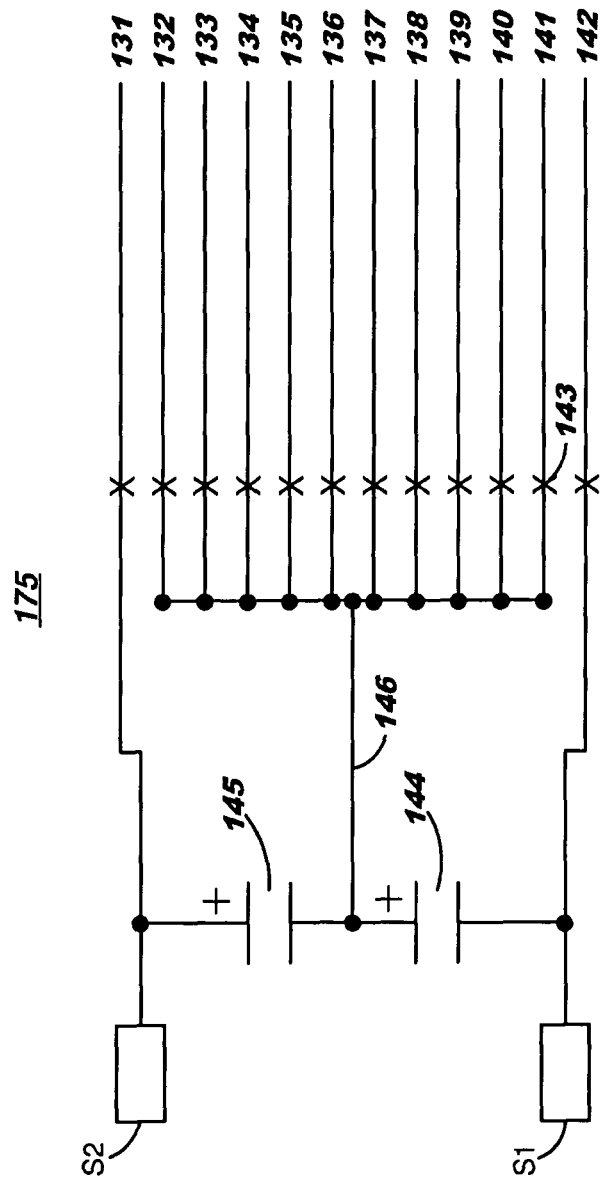
FIG. 4 shows an exemplary selection of electrodes serving as shield electrodes tied to a common node and other electrodes providing sensing or stimulation.

FIG. 4 shows an arrangement 175 in which an exemplary selection of electrodes 132-141 serving as shield electrodes tied to a common node 146 and other electrodes 131, 142 providing sensing or stimulation. In this figure, it is assumed that particular crosspoint switches (fabric 124 in FIG. 3) are closed to bring about the connections such as 143 in FIG. 4. (Common node 146 is like node 111 in FIG. 3.) (Only the active crosspoint connections are shown in FIG. 4, for clarity, and the other possible crosspoint connections are omitted for clarity.) In the arrangement 175 the circuitry 125 (FIG. 3) is composed of capacitors 144, 145 which define node 146 to fall about halfway between conductors S1, S2. Preferably the capacitors 144, 145 are matched or nearly matched in value. The arrangement 175 is able to bring about the results portrayed in FIG. 2E, where driven electrodes 131, 142 correspond to electrodes 92, 93 in FIG. 2E. Shield electrodes 132-141 correspond to shield electrodes 91 in FIG. 2E.

Figure 5:
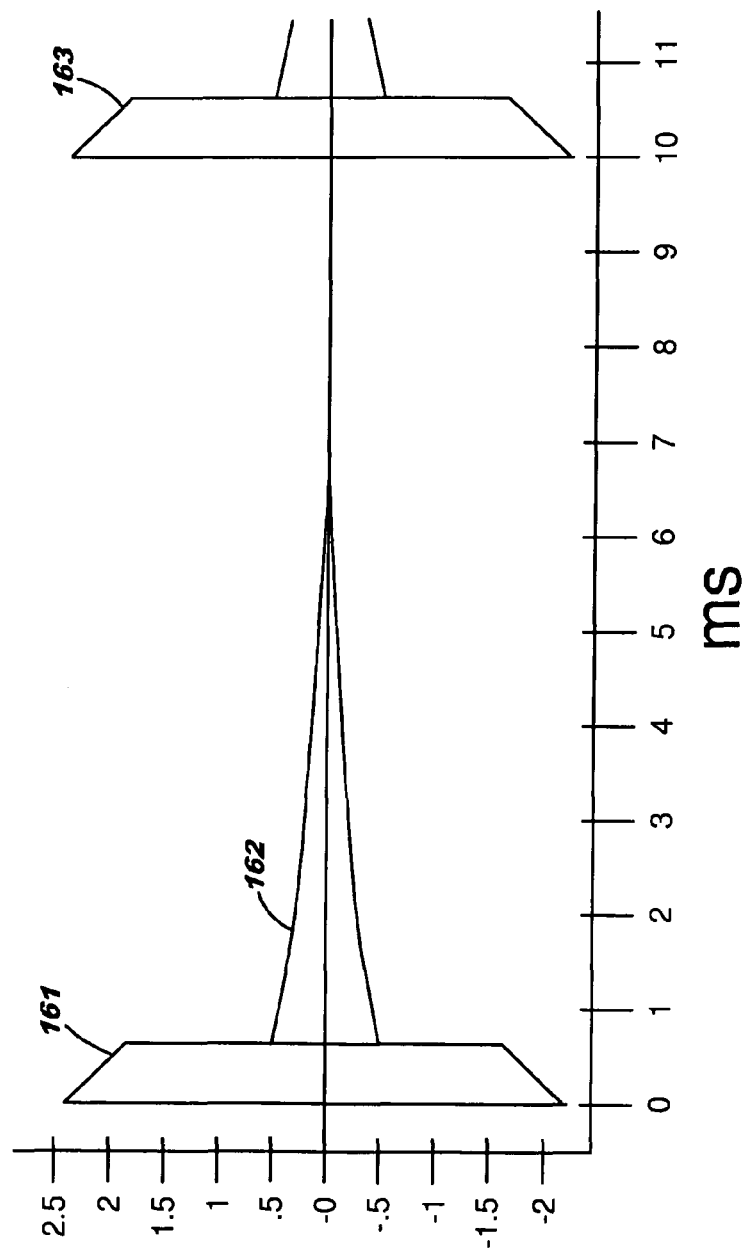
FIG. 5 shows a model for a stimulation pulse and a dissipation of the imposed pulse.

FIG. 5 shows a model for a stimulation pulse and a dissipation of the imposed pulse, in a shielded arrangement such as discussed above. A pulse 161 may persist for half a microsecond, the pulse here being bipolar, with one driven electrode driven to slightly over two volts, and the other driven electrode pulled down to slightly less than minus two volts. When the pulse ends, the stimulus fades (as modeled by shape 162). On one tissue and geometry model the stimulus has faded nearly to nothing within five or six milliseconds. Later another pulse 163 may happen.

Figure 6A:
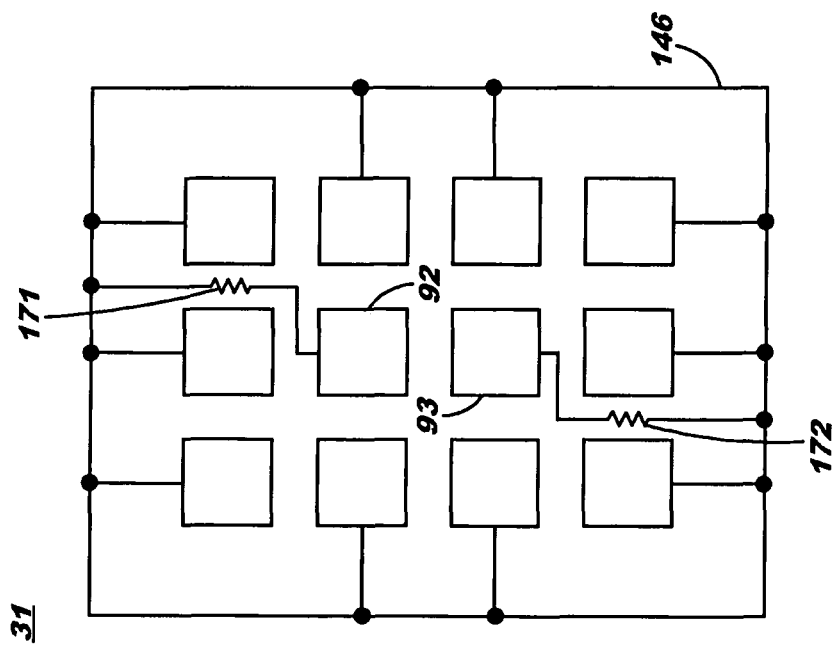
FIG. 6A shows an impedance model for a twelve-position electrode array in animal tissue.

FIG. 6A shows an impedance model for a twelve-position electrode array 31 in animal tissue. In this model it is assumed that electrodes 92, 93 are driven (as in FIG. 2E) and that the remaining electrodes serve as shield electrodes (as electrodes 91 in FIG. 2E). The shield electrodes are tied together electrically at node 146 (as in FIG. 4). Each of the driven electrodes 92, 93 is modeled as have some impedance 171, 172 through the adjacent tissue of the animal.

Figure 6B:
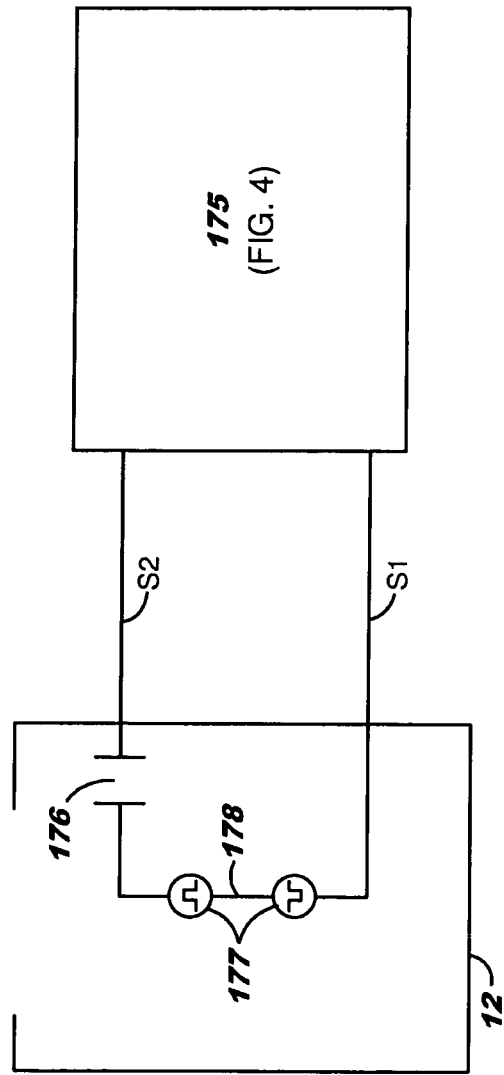
FIG. 6B shows an exemplary driver configuration in a "can" for driving electrodes such as are portrayed above.

FIG. 6B shows an exemplary driver configuration 205 in a "can" 12 for driving electrodes such as are portrayed above in circuitry 175 (FIG. 4). Positive-going drive and negative-going drive 177 are capacitively coupled (through capacitor 176) to the lead conductors S1, S2 as shown. A reference 178 may be defined within the can 12, and in some applications might be tied to a metal housing of the can 12 and thus be coupled to the animal, although most of the teachings of the invention offer their benefits even if the point 178 is floating relative to everything else in the figure.

FIGS. 7A, 7B, and 7C show exemplary positioning of integrated circuitry chips relative to conductors of a lead. FIG. 7A shows a single IC chip O bonded to conductors 181 (for example conductors S1, S2). A lumen 185 helps to guide the lead into place and may later be withdrawn. FIG. 7B shows two IC chips O, P bonded back-to-back to conductors 181 and tied together by physical material as shown. FIG. 7C shows four IC chips O, P, L, and F bonded in a square to conductors 181 and tied together by physical material as shown.

The arrangement of FIG. 7A provides (for example) 12 electrodes at each electrode position along the length of the lead. The arrangement of FIG. 7B provides 24 electrodes at each electrode position along the length of the lead. The arrangement of FIG. 7C provides 48 electrodes at each electrode position along the length of the lead.

Such arrangements permit great versatility in the use of the lead after it has been implanted. Various combinations of electrodes can be tried, even by trial and error, until such time as some combination is found that permits a particular specific desired stimulus in some physical location within the tissue, or that permits sensing of electrical activity in some physical location within the tissue. In this way it may be possible to avoid or to postpone having to remove and re-insert a lead in a particular tissue area.

Figure 8:
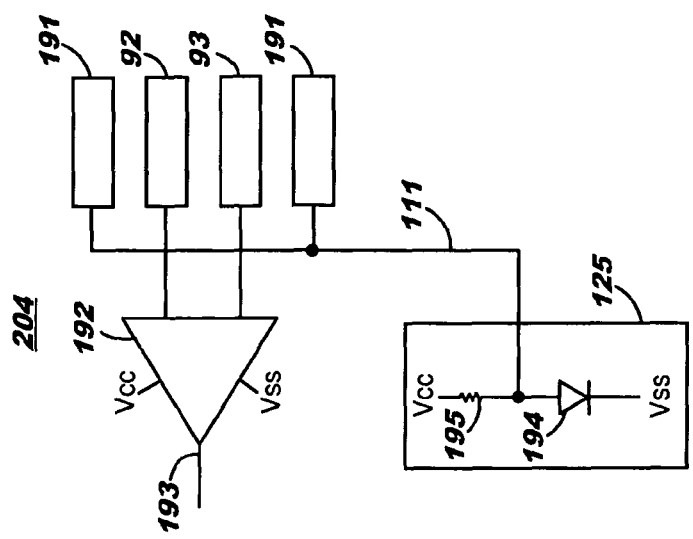
FIG. 8 shows an exemplary sensing arrangement using shield electrodes.

FIG. 8 shows an exemplary sensing arrangement 204 using shield electrodes 191. In this arrangement two particular electrodes 92, 93 (see again FIG. 2E) are connected with inputs of differential amplifier 192. The amplifier 192 has an output 193 which is communicated to electronics external to the electrode location (for example to can 12, omitted for clarity in FIG. 8). As may be seen in this figure, the node 111 is again tied to circuitry 125, which in this case provides a diode drop 194 away from one supply line Vss and is urged toward the other supply line Vcc by resistor 195. (Here, Vcc and Vss may be the same as, or may be derived from, lines S1 and S2.) For this arrangement 204, the switching fabric 124 (FIG. 3) will have two more columns, as discussed above in connection with FIG. 3.

Onsite signal processing, as described herein, can reduce noise.

Figure 9A:
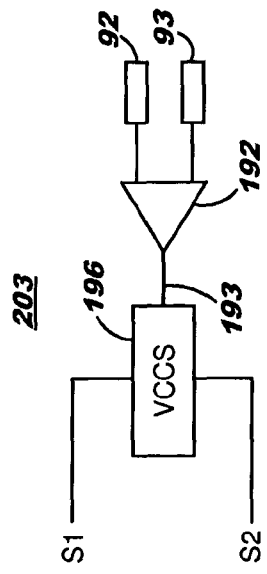
FIG. 9A shows an exemplary drive mechanism for the use of currents to communicate sensed voltages.

FIG. 9A shows an exemplary drive mechanism 203 for the use of currents to communicate sensed voltages. Electrodes and differential amplifier are as in FIG. 8, but the amplified signal 193 drives a voltage-to-current converter 196, which in turn drives particular levels of current in the lines S1, S2. This current is later sensed in the can 12 using, for example, the exemplary sensing mechanism 202 of FIG. 9B. The current passes through resistor 198 and the developed IR drop reaches differential amplifier 197.

Figure 9B:
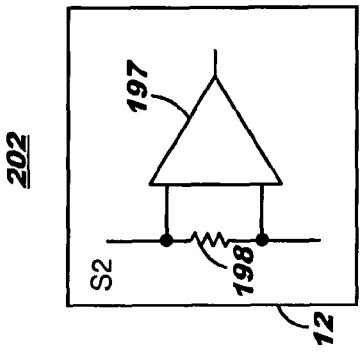
FIG. 9B shows an exemplary sensing mechanism usable in a "can" for making use of currents such as portrayed in the previous figure.

It will be appreciated that it is not crucial to the invention that the current sensing approach of FIG. 9B be employed. For example a standard current-to-digital converter could be used.

Figure 9C:
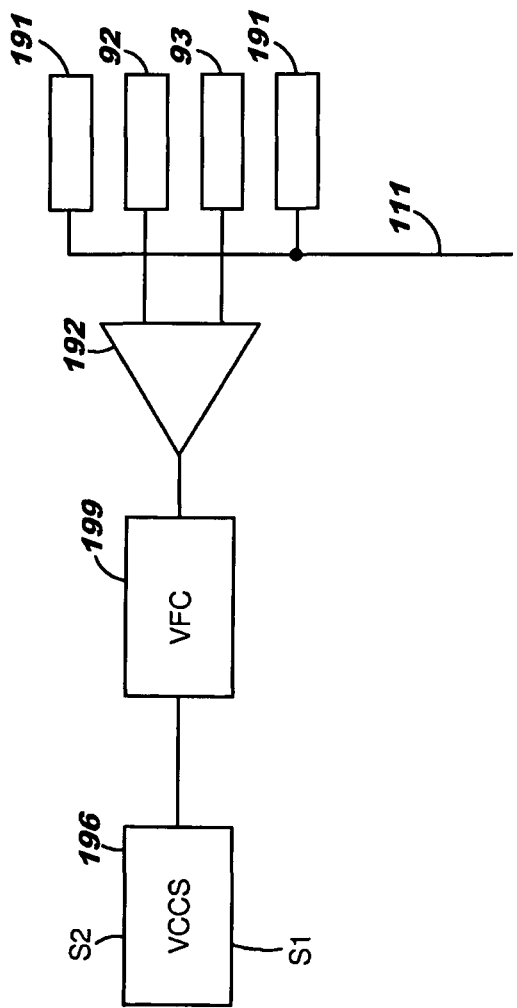
FIG. 9C shows an exemplary drive mechanism for the use of phase or frequency modulations to communicate sensed voltages.

It will also be appreciated that any of several other approaches could be employed to communicate sensed electrical activity to the external electronics such as can 12. FIG. 9C shows an exemplary drive mechanism 201 for the use of phase or frequency modulations to communicate sensed voltages. A voltage-to-frequency converter 199 can drive current driver 196 to communicate sensed-data information by means of a frequency modulation. Alternatively a phase modulation could be used.

Figure 9D:
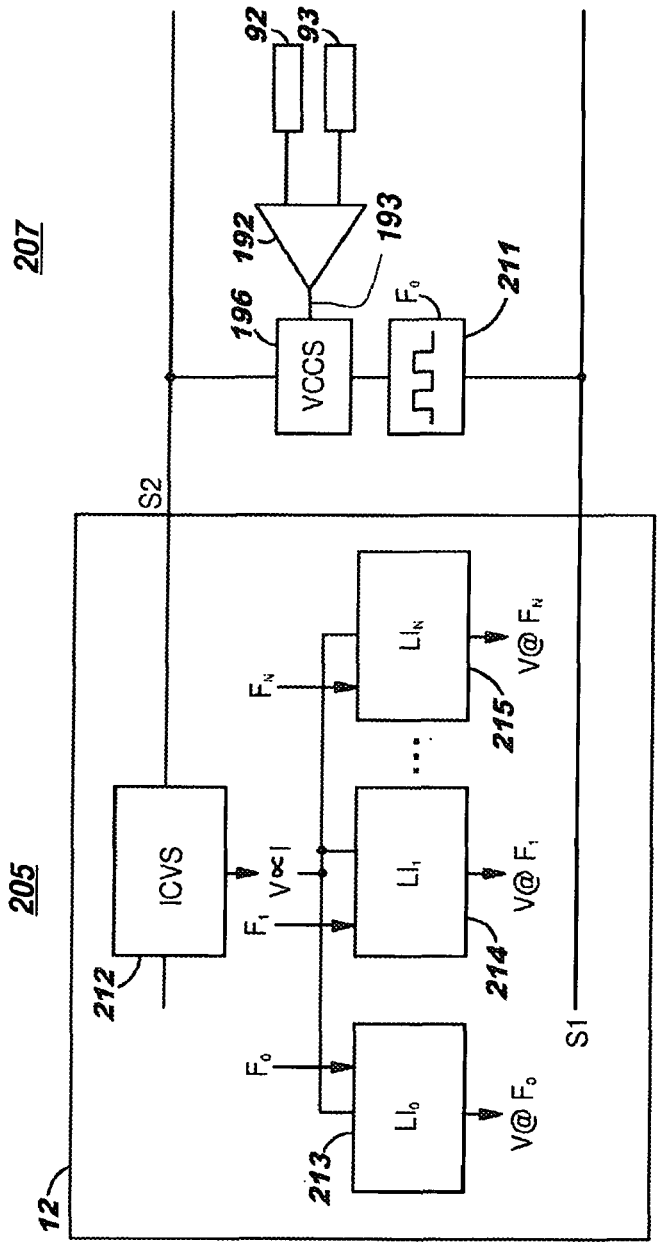
FIG. 9D shows an exemplary drive mechanism for the use of modulation functions to communicate sensed voltages, and an exemplary demodulation mechanism usable in a "can" for making use of modulations such as portrayed in the previous figure.

FIG. 9D shows an exemplary drive mechanism 207 for the use of modulation functions to communicate sensed voltages, and an exemplary demodulation mechanism 206 usable in a can 12 for making use of modulations such as portrayed in the previous figure. A modulation function f0 modulates at modulator 211. Other electrode-sensing arrays, omitted for clarity in FIG. 9D, use other modulation functions f1 through fn in corresponding fashion. In the can 12, a demodulation mechanism uses demodulators 213, 214, 215 with the same functions f0, f1, fn to derive distinct voltages, each of which is proportional to a sensed voltage such as at electrodes 92, 93.

In one embodiment of the invention, a method is carried out so as to apply an electrical pulse to, or to sense electrical activity at, a first region of tissue in an animal. A first array of electrodes is provided at the first region of tissue, the array disposed upon a respective surface. The first array comprises respective first and second electrodes disposed upon the respective surface. The first array further comprises a plurality of respective third electrodes (shield electrodes) also disposed upon the respective surface and surrounding the respective first and second electrodes. The first array of electrodes is electrically selectively connected via a lead to electronics located external to the first array of electrodes, such as the can 12. The lead comprises at least one electrical conductor and for example may have two conductors. Selective connections are made so that sensing or driving circuitry is connected to the first and second electrodes. The shield electrodes are configured to serve as an electrical shield for the first and second electrodes through conductive coupling with tissue nearby thereto.

The surface carrying the electrodes can be substantially planar, if for example it is a surface of an integrated circuit. The surface would not have to be planar, however, and might for example be convex.

The number of shield electrodes might be as few as two, might be six, and in the embodiments discussed herein the number of shield electrodes may be ten.

The circuitry 125 at the common node 111 of the shield electrodes can bias the shield electrodes at a stable voltage between the positive and negative power supplies. The stable voltage between the positive and negative power supplies may be defined to be at least a diode drop away from either of the power supplies. The circuitry may further establish the stable voltage at least two diode drops away from the potential of the substrate of the integrated circuit.

Sensed electrical activity may be converted to a digital signal, the digital signal thereby carried on an electrical conductor or conductors of the lead to the electronics (for example can 12). Alternatively an envelope modulation (AM) may be employed.

In many embodiments there will be two or more (and likely a multiplicity of) electrode locations, each having an array of electrodes including shielding electrodes. In such cases, addressing techniques are employed to permit carrying out stimulation at one location and later at a different location. Other techniques such as the multiplexing techniques mentioned above may be employed to permit sensing of electrical activity at each of two or more locations. The multiplexing may be for example time-domain multiplexing or frequency-domain multiplexing.

One embodiment of the invention this comprises the use of an array of multiplexed electrodes for applying an electrical pulse to, or for sensing electrical activity at, a region of tissue in an animal. A first array is provided at a first region of tissue. The multiplexing permits each electrode to be electrically isolated, connected to at least one conductor within the lead, or connected to a floating node connected to other electrodes in the array. Each electrode can likewise be electrically connected to at least one input of a sensing circuit. Each electrode can likewise be electrically connected to a current source. In a typical arrangement, at least one electrode that is enabled to the floating node is adjacent to at least one electrode that is enabled to a conductor in the lead. Likewise it can happen that at least one electrode that is enabled to the floating node is adjacent to at least one electrode that is enabled to an input of a sensing circuit.

In an exemplary arrangement, a first electrode can be enabled to a first conductor in the lead, a second electrode can be enabled to a second conductor in the lead, and at least two additional electrodes on the surface are enabled to the floating node.

Returning to the circuitry 125 (FIG. 3), the floating node 111 may be capacitively coupled to at least one conductor in the lead. Or the floating node may be capacitively coupled to two conductors in the lead using two substantially equivalent capacitors. Or the floating node may be electrically connected to at least one conductor in the lead and that conductor is electrically isolated from the drive circuitry. The floating node may be biased to be at least one diode drop away from sensor supply voltages.

It will be appreciated that in use with animals, a medical carrier will typically comprise multiple such electrode arrays connected to said at least one conductor in the lead.

When electrical activity is being measured, as discussed above in connection with FIGS. 8, 9A, 9C, and 9D, a sequence of steps may be carried out in which a first value is stored that is indicative of the sensed phenomena. Later a second value is stored indicative of the sensed phenomena at a later time. The two values may be subtracted so that all that needs to be communicated is the difference between the two values.

A typical sequence of steps may be to selecting first electrodes from an array for use to sense or stimulate, and selecting second shield electrodes from the array connected to a floating node, observing phenomena relating to the animal and noting the phenomena observed in connection with the selected electrodes. Next a different set of electrodes from the array are used to sense or stimulate, and fourth shield electrodes from the array are connected to a floating node, and again phenomena are observed relating to the animal and noting the phenomena observed in connection with the selected electrodes. After some experimentation, some combination of electrodes may be selected and may be employed for some interval thereafter, and during the interval, sensing or stimulation may be carried out. The tissue may be neural tissue.

A removable distal accelerometer or motion sensor may be used to help in the treatment of movement disorders such as Parkinson's or dystonia.

Methods of Conveying Sampled Analog Signals from Lead IC to the Can.

Referring to FIG. 8, shield electrodes 191 bias input electrodes 92, 93 and reduce common-mode signals, making input more sensitive to near-field signals and less sensitive to distant ones. The shield electrodes 191 are biased one or two diode drops 194 above the substrate 125 potential (or below the substrate 125 potential, if the substrate 125 is most positive.).

This idea is to bias the shield electrodes 191 at a stable voltage between Vcc and Vss, ideally at least a diode drop from either. The shield electrodes 191 will then act to reduce the common-mode signal that reaches electrodes 92 and 93 as amplified by the differential amp 192.

First Method of Conveying Sampled Analog Signals from Lead IC to the Can.

Referring to FIG. 9A, what is shown is some of the circuitry disposed on the Lead IC 203. One differential amplifier 192 is selected at a time, then the potential difference between electrodes 92 and 93 is converted to a current signal proportional to that potential difference at output leads S1 and S2.

Second Method of Conveying Sampled Analog Signals from Lead IC to the Can.

Referring to FIG. 9B, what is shown is some circuitry within the can. The circuit uses a current-controlled voltage source and is similar to existing talk-back circuits. Alternatively, the can may directly employ a current-to-digital converter. In this embodiment, the signal is amplified 197 and converted to a current on the Lead IC 202. In the can, the current is sampled to extract the analog signal as the tissue impedance 198 varies while the voltage on S2 is held constant. The output voltage signal from the amp 197 is proportional to the voltage drop across 198.

Third Method of Conveying Sampled Analog Signals from Lead IC to the Can.

Referring to FIG. 9B, in this embodiment, multiple amplifiers are used to multiplex analog signals down a two-wire bus. It is envisioned that time multiplexing would commonly be used.

This method is similar to the Second Method described above, but is extended to multiple locations (satellites), each being time multiplexed. Each location's S1 and S2 leads are clocked. For example, assume eight locations at 1 kHz sampling. A 10-kHz signal (with out-of-phase, pulsating DC square-wave signals on S1 and S2, respectively) is forced on S1 and S2. On each Lead IC 202, a different timeslot following a "start" command is pre-set on each Lead IC 202. Satellite 0 is assigned the first timeslot, Satellite 1 is assigned the second timeslot, etc. Each Lead IC 202 has a Power Regulator that actively rectifies the S1 and S2 voltage. The analog amplifiers 197 are enabled on each Lead IC 202 only when that Lead IC's 202 timeslot is enabled. Otherwise, the circuit works like that described in the Second Method discussed above. This methodology, however, necessarily results in a more complex can circuitry design, which is needed to track timeslots, etc. In addition, this method requires a "Start Analog Multiplex" command be used as an extension of an existing communication protocol.

Fourth Method of Conveying Sampled Analog Signals from Lead IC to the Can.

Referring to FIG. 9B, this method is a variation of the Third Method discussed above. In this variation, the "noise" of the amplifier's 197 current consumption is eliminated. In the Third Method described above, the current on leads S1 and S2 equals the sum of the amplifier's 197 current draw and the forced current that is proportional to the sampled voltage. In this variation, the total current drawn by the enabled Lead IC 202 is proportional to the differential voltage across the sample.

Referring to FIG. 9A, in a second variation of this Fourth Method, the amplifier 192 samples, amplifies, and holds the resulting voltage 193 on a capacitor. The amplifier 192 then shuts down, and the current on S1 and S2 is only the current through the Voltage-Controlled Current Source (VCCS).

Fifth Method of Conveying Sampled Analog Signals from Lead IC to the Can.

Referring to FIG. 9C, this embodiment is a variation of the Third Method described above, and discloses multiplexing in the frequency domain. In this embodiment, each Lead IC 201 is given a dedicated frequency 199. The can provides a stable voltage across S1 and S2, but samples the current drawn through S1 an S2. Thus, each thus each Lead IC 201 converts the amplified voltage into a frequency and then pulls a constant-amplified sinusoidal current through the VCCS with, for example, a sinusoid-like wave centered on the frequency. (However, a square wave can be acceptable as well.) Essentially, the phase of the carrier wave is being modulated. These carrier frequencies would likely be related to the clocking frequency. For example, the frequency on Satellite 0, would be approximately 10 times the clock frequency, Satellite 1 would be approximately 11 times the clock frequency, etc.

Sixth Method of Conveying Sampled Analog Signals from Lead IC to the Can.

Referring to FIGS. 9C and 9D, this embodiment is a variation of the Fifth Method described above. In this variation, the frequency "broadcast" by each Lead IC is fixed. The amplitude pulled down by each Lead IC varies with the sampled signal. A lock-in amplifier (213, 214, 215, etc.) in the can for each frequency recovers each transmitted signal, either digitally or via multiple lock-ins. As in the Fifth Method described above, the frequency signals can take the form of a sinusoidal-like wave or as a square wave 211. f0 is approximately 1/10 of the clock carrier frequency. For example, if the carrier frequency is approximately 100 kHz, then f0 would be approximately 10 kHz, with the signal itself being approximately 1 kHz.

Seventh Method of Conveying Sampled Analog Signals from Lead IC to the Can.

Referring to FIGS. 9C and 9D, this embodiment is a variation of the Sixth Method in which each enabled Lead IC amplifies the signal as in the First Method described above, and employs an analog-to digital converter (ADC) to convert the voltage into a binary number. This number is then sent back to the Can using a variation of existing talk-back circuitry. For example, each Lead IC would be allocated a certain range of clock cycles, during which a given Lead IC transmits back to the can the data that had just been gathered.

For example, on one clock cycle, the signals are amplified and converted to a digital signal on all Lead ICs. On the next clock cycle, Satellite 0 communicates its data, then on the immediately following clock cycle, Satellite 1 communicates its data, etc.

In this way, the power consumption caused by the amplification and ADC process are only realized for a short period of time. The balance of the communication then occurs as with existing communication protocols.

Those skilled in the art will have no difficulty devising myriad obvious improvements and variations upon the invention, all of which are intended to be encompassed within the claims that follow.

The invention claimed is:

1. Apparatus for applying an electrical pulse to, or for sensing electrical activity at, a first region of tissue in an animal, the apparatus comprising:

a first array of electrodes disposed upon a respective surface, the first array comprising respective first and second electrodes disposed upon the respective surface, the first array further comprising a plurality of respective third electrodes also disposed upon the respective surface and surrounding the respective first and second electrodes;

wherein the first array of electrodes is electrically selectively connected via a lead to electronics located external to the first array of electrodes, the lead comprising at least one electrical conductor;

the selective connections of the electrodes comprising sensing or driving circuitry connecting the first and second electrodes with the at least one electrical conductor, and further comprising circuitry disposing the third electrodes to serve as an electrical shield for the first and second electrodes through conductive coupling with tissue nearby thereto.

2. The apparatus of claim 1 wherein the selective connections of the electrodes comprises driving circuitry.

3. The apparatus of claim 1 wherein the selective connections of the electrodes comprises sensing circuitry.

4. The apparatus of claim 1 wherein the sensing circuitry comprises a differential amplifier receiving the first and second electrodes as inputs, and providing an output to the at least one electrical conductor, whereby sensed electrical activity is communicated to the electronics external to the array of electrodes.

5. The apparatus of claim 1 wherein the respective surface is substantially planar.

6. The apparatus of claim 1 wherein the respective surface is convex.

7. The apparatus of claim 1 wherein the number of third electrodes is at least six.

8. The apparatus of claim 7 wherein the number of third electrodes is ten.

9. The apparatus of claim 1 wherein the first array receives positive and negative power supplies, and wherein the circuitry selectively connecting the third electrodes to the at least one electrical conductor comprises circuitry biasing the third electrodes at a stable voltage between the positive and negative power supplies.

10. The apparatus of claim 9 wherein the circuitry selectively connecting the third electrodes to the at least one electrical conductor establishes the stable voltage between the positive and negative power supplies at least a diode drop away from either of the power supplies.

11. The apparatus of claim 10 wherein the circuitry selectively connecting the electrodes defines a substrate, and wherein the substrate has a potential, and wherein the circuitry selectively connecting the third electrodes to the at least one electrical conductor further establishes the stable voltage at least two diode drops away from the potential of the substrate.

12. The apparatus of claim 3 wherein the sensed electrical activity as voltage is converted to current, the current thereby carried on the at least one electrical conductor to the electronics, the electronics disposed to measure the current.

13. The apparatus of claim 3 wherein the sensed electrical activity as voltage is converted to a digital signal, the digital signal thereby carried on the at least one electrical conductor to the electronics, the electronics disposed to detect the digital signal.

14. The apparatus of claim 13 wherein the carriage of the digital signal on the at least one electrical conductor is performed by means of an envelope modulation.

15. The apparatus of claim 1 further comprising a second array of electrodes disposed upon a respective surface, the second array comprising respective first and second electrodes disposed upon the respective surface, the second array further comprising a plurality of respective third electrodes also disposed upon the respective surface and surrounding the first and second electrodes;
    wherein the second array of electrodes is electrically selectively connected via the lead to the electronics located external to the first array of electrodes, the electronics located external to the first array of electrodes also located external to the second array of electrodes;
    the selective connections of the electrodes comprising sensing or driving circuitry connecting the first and second electrodes with the at least one electrical conductor, and further comprising circuitry disposing the third electrodes to serve as an electrical shield for the first and second electrodes through conductive coupling with tissue nearby thereto.

\* \* \* \* \*